(12) United States Patent
Ikeshita et al.

(10) Patent No.: US 6,735,276 B2
(45) Date of Patent: May 11, 2004

(54) SAMPLE PREPROCESSING SYSTEM FOR A FLUORESCENT X-RAY ANALYSIS AND X-RAY FLUORESCENCE SPECTROMETRIC SYSTEM USING THE SAME

(75) Inventors: Akihiro Ikeshita, Takatsuki (JP); Motoyuki Yamagami, Takatsuki (JP)

(73) Assignee: Rigaku Industrial Corporation, Osaka (JP)

( * ) Notice: Subject to any disclaimer, the term of this patent is extended or adjusted under 35 U.S.C. 154(b) by 28 days.

(21) Appl. No.: 10/244,384

(22) Filed: Sep. 17, 2002

(65) Prior Publication Data

US 2003/0053589 A1 Mar. 20, 2003

(30) Foreign Application Priority Data

Sep. 18, 2001 (JP) ......................................... 2001-282907

(51) Int. Cl.[7] ........................ G01N 23/223; B05C 11/02; B08B 3/04
(52) U.S. Cl. ........................ 378/45; 118/52; 118/663; 118/719; 134/1.3; 134/33; 134/34
(58) Field of Search ........................ 378/44, 45; 118/52, 118/663, 719; 134/1.3, 33, 34

(56) References Cited

U.S. PATENT DOCUMENTS

| | | | | |
|---|---|---|---|---|
| 5,395,446 A | * | 3/1995 | Kageyama et al. | 118/52 |
| 5,527,707 A | * | 6/1996 | Fukazawa | 436/72 |
| 5,742,658 A | * | 4/1998 | Tiffin et al. | 378/44 |
| 5,916,824 A | * | 6/1999 | Mayuzumi et al. | 438/753 |
| 6,043,486 A | * | 3/2000 | Hossain | 250/252.1 |
| 6,164,133 A | * | 12/2000 | Watanabe | 73/432.1 |
| 6,173,036 B1 | * | 1/2001 | Hossain et al. | 378/45 |
| 6,174,740 B1 | * | 1/2001 | Ohta et al. | 438/14 |
| 6,182,675 B1 | * | 2/2001 | Naka et al. | 134/61 |
| 6,381,303 B1 | * | 4/2002 | Vu et al. | 378/46 |
| 6,611,577 B1 | * | 8/2003 | Yamagami | 378/48 |
| 2003/0084926 A1 | * | 5/2003 | Watanabe | 134/33 |

* cited by examiner

*Primary Examiner*—David V. Bruce
*Assistant Examiner*—Allen C. Ho
(74) *Attorney, Agent, or Firm*—Birch, Stewart, Kolasch & Birch, LLP

(57) ABSTRACT

A sample preprocessing system for a fluorescent X-ray analysis includes a sample preprocessing apparatus for retaining on a surface of a substrate a substance to be measured that is found on the surface of the substrate, after such substance has been dissolved and subsequently dried, a transport apparatus for transporting the substrate, and a control apparatus for controlling the sample preprocessing apparatus and the transport apparatus. The control apparatus 60 after having confirmed that the pressure difference between inside and outside of the apparatus 10 (20, 30) and the concentration of the reactive gas within the apparatus are within a predetermined range causes automatically opening and closing shutters 21*a*, 27 and 31*a* to thereby avoid a possible corrosion of the apparatuses positioned outside the sample preprocessing apparatus while increasing the service lifetime thereof.

4 Claims, 5 Drawing Sheets

SAMPLE PREPROCESSING SYSTEM FOR A FLUORESCENT X-RAY ANALYSIS AND X-RAY FLUORESCENCE SPECTROMETRIC SYSTEM USING THE SAME

BACKGROUND OF THE INVENTION

1. Field of the Invention

The present invention relates to a sample preprocessing system for a fluorescent X-ray analysis, which system includes a sample preprocessing apparatus for retaining on a surface of a substrate a substance to be measured that is found on the surface of the substrate, after such substance has been dissolved and subsequently dried, a transport apparatus for transporting the substrate, and a control apparatus for controlling the sample preprocessing apparatus and the transport apparatus, and an X-ray fluorescence spectrometric system utilizing such sample preprocessing system.

2. Description of the Prior Art

In this type of the X-ray fluorescence spectrometric system, it has been suggested to facilitate an easy operation of the system as a whole. See, for example, the Japanese Patent Application No. 2001-270604. According to the suggested X-ray fluorescence spectrometric system, a vapor phase decomposing apparatus and a sample recovery apparatus that constitute the sample preprocessing apparatus has its own automatically opening and closing shutter adapted to be properly opened or closed by a control apparatus when the substrate is to be transported into or out of the apparatus. While a reactive gas such as hydrogen fluoride is employed within the sample preprocessing apparatus, during a normal operation the automatically opening and closing shutters will not be opened when a high concentration of the reactive gas is present within the apparatus and, since even if they were to be opened, the apparatus has an inside pressure set to be lower than the pressure outside the apparatus, there is no possibility that the reactive gas within the apparatus may flow out of the apparatus to such an extent as to result in adverse influence on other apparatuses.

However, when by reason of, for example, an erroneous operation the automatically opening and closing shutter is opened while a certain concentration of the reactive gas is present within the apparatus and the inside pressure of the apparatus is not so low as compared with the pressure outside the apparatus, the reactive gas will flow outwardly of the apparatus and, as a result thereof, there is the possibility that the transport apparatus and/or the X-ray fluorescence spectrometer positioned outside the apparatus will be corroded with the service lifetime thereof consequently reduced.

SUMMARY OF THE INVENTION

The present invention has been devised with a view to substantially eliminating the inconveniences inherent in the conventional system discussed above and is intended to provide a sample preprocessing system for a fluorescent X-ray analysis, which system includes a sample preprocessing apparatus for retaining on a surface of a substrate a substance to be measured that is found on the surface of the substrate, after such substance has been dissolved and subsequently dried, a transport apparatus for transporting the substrate, and a control apparatus for controlling the sample preprocessing apparatus and the transport apparatus, wherein corrosion prevention and increase of the service lifetime are made in the transport apparatus or the like that is positioned outside the sample preprocessing apparatus.

Another important object of the present invention is to provide an X-ray fluorescence spectrometric system utilizing the sample preprocessing system of the type discussed above.

In order to accomplish the foregoing objects, the present invention in one aspect thereof provides a sample preprocessing system for a fluorescent X-ray analysis, which system includes a vapor phase decomposing apparatus, a sample recovery apparatus, a transport apparatus, and a control apparatus, all of which are discussed below. It is to be noted that the vapor phase decomposing apparatus and the sample recovery apparatus altogether constitute a sample preprocessing apparatus.

The vapor phase decomposing apparatus is operable to retain on a surface of a substrate a substance to be measured that is found on the surface of the substrate or a substance to be measured that is found on a surface of a film formed on the surface of the substrate or within the film, after such substance has been dissolved by a reactive gas and has subsequently been dried, in a decomposing chamber. The sample recovery apparatus is operable to drop a solution on the substrate having the surface on which the substance to be measures exists, to move the solution on the substrate surface while being retained by a holder, and to retain the substance to be measured on the substrate surface after having been recovered in the solution and then dried, in a recovery chamber. The transport apparatus is operable to transport the substrate from the decomposing chamber towards the recovery chamber. The control apparatus controls the vapor phase decomposing apparatus, the sample recovery apparatus, and the transport apparatus. A set of the vapor phase decomposing apparatus and the sample recovery apparatus includes an automatically opening and closing shutter, a differential pressure detecting means for detecting a pressure difference between inside and outside of the set and a concentration detecting means for detecting a concentration of the reactive gas within the set. The control apparatus is operable to open the automatically opening and closing shutter after it has ascertained that the pressure difference detected by the differential pressure detecting means and the concentration detected by the concentration detecting means are within respective predetermined ranges.

According to the present invention, since the control apparatus opens the automatically opening and closing shutter after it has ascertained that the pressure difference between inside and outside of the sample preprocessing apparatus detected by the differential pressure detecting means and the concentration of the reactive gas within the sample preprocessing apparatus detected by the concentration detecting means are within the respective predetermined ranges, there is no possibility that the reactive gas may flow from inside the sample preprocessing apparatus to the outside and, therefore, corrosion prevention and increase of the service lifetime of the transport apparatus and others that are positioned outside can be sufficiently attained.

The present invention in another aspect thereof provides an X-ray fluorescence spectrometric system including the sample preprocessing system for the fluorescent X-ray analysis discussed above, in combination with an X-ray fluorescence spectrometer for irradiating the substance to be measured, that is retained on the surface of the substrate by the vapor phase decomposing apparatus or the sample recovery apparatus, with primary X-rays to excite the substance to be measured and for subsequently measuring intensities of fluorescent X-rays emitted therefrom as a result of the excitation. In this X-ray fluorescence spectrometric system, the transport transports the substrate from the decomposing chamber towards the X-ray fluorescence spectrometer and also from the recovery chamber towards the X-ray fluorescence spectrometer, and the control apparatus controls the X-ray fluorescence spectrometer as well. Even with the X-ray fluorescence spectrometric system of the present invention, effects similar to those afforded by the sample preprocessing system of the present invention can be obtained.

BRIEF DESCRIPTION OF THE DRAWINGS

In any event, the present invention will become more clearly understood from the following description of preferred embodiments thereof, when taken in conjunction with the accompanying drawings. However, the embodiments and the drawings are given only for the purpose of illustration and explanation, and are not to be taken as limiting the scope of the present invention in any way whatsoever, which scope is to be determined by the appended claims. In the accompanying drawings, like reference numerals are used to denote like parts throughout the several views, and:

DETAILED DESCRIPTION OF THE EMBODIMENT

Figure 1A:
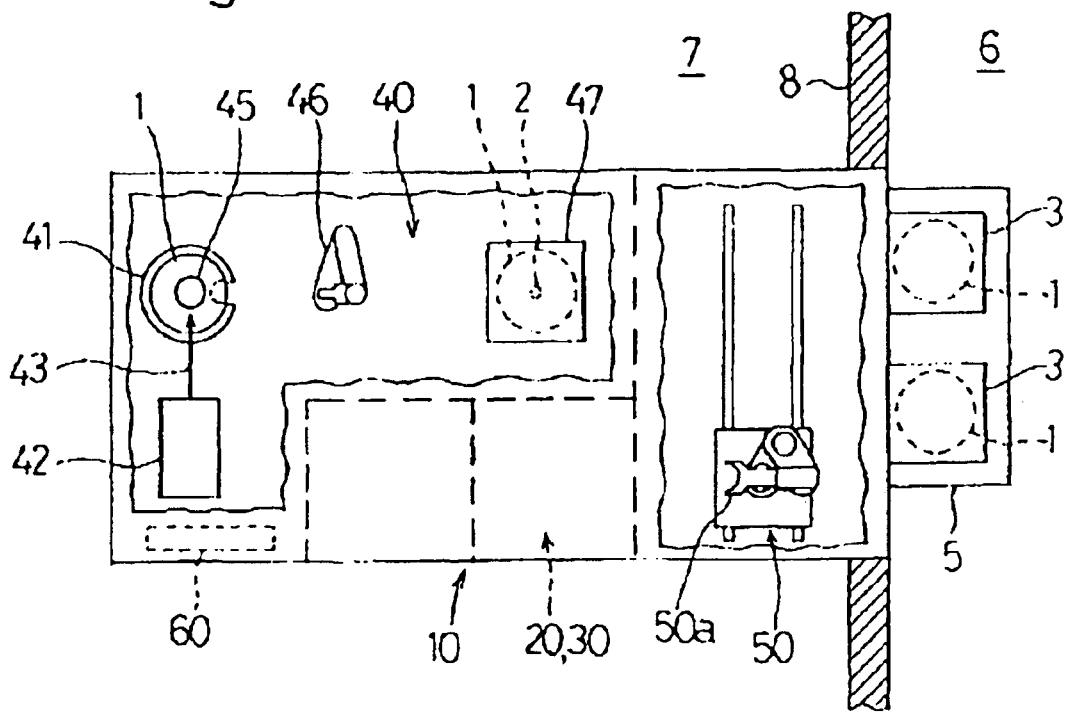
FIG. 1A is a schematic plan view, with portions cut out, of an X-ray fluorescence spectrometric system according to a preferred embodiment of the present invention.
Figure 1B:
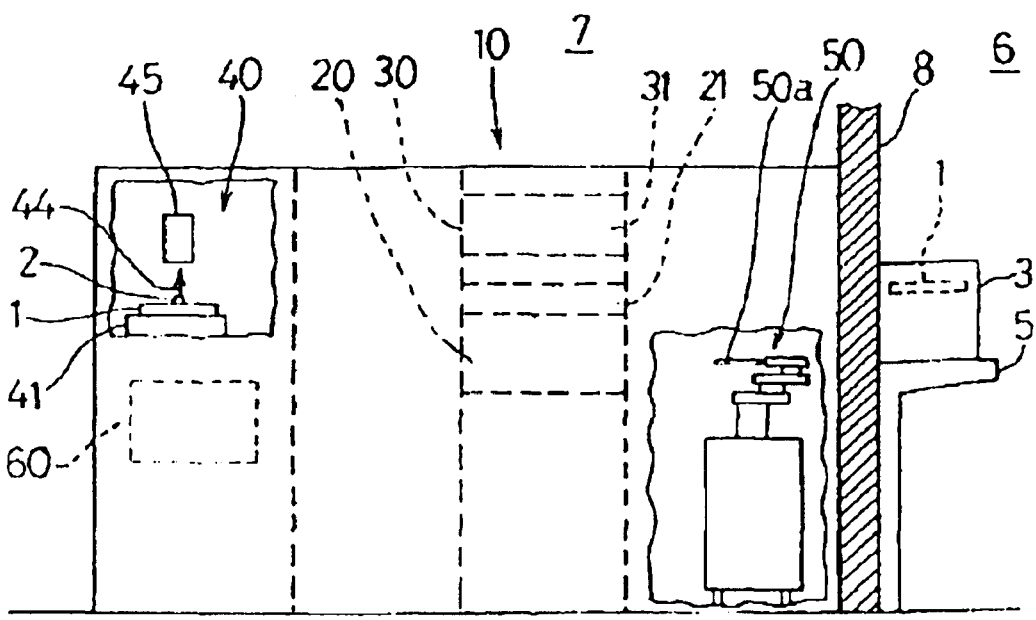
FIG. 1B is a schematic front elevational view, with portions cut out, of the X-ray fluorescence spectrometric system shown in FIG. 1A.

The structure of an X-ray fluorescence spectrometric system according to a preferred embodiment of the present invention will now be described. Referring first to FIGS. 1A and 1B, the X-ray fluorescence spectrometric system includes a sample preprocessing apparatus 10 having a vapor phase decomposing apparatus 20 and a sample recovery apparatus 30, an X-ray fluorescence spectrometer 40 having an X-ray source 42 for projecting primary X-rays 43 towards a substance 2 to be measured, which is placed on a substrate 1 supported on a sample table 41, so as to irradiate the substance 2 to be measured and a detecting means 45 for detecting fluorescent X-rays emitted from the substance 2 to be measured as it is excited by the primary X-rays 43, and a transport apparatus 50 for transporting the substrate 1 from the sample preprocessing apparatus 10 towards the X-ray fluorescence spectrometer 40.

In the illustrated embodiment, the X-ray fluorescence spectrometer 40 employed is of a total reflection type in which the primary X-rays emitted from the X-ray source 42 impinge upon the sample at a minute angle of incidence. The X-ray source 42 employed therein includes an X-ray tube, a spectroscopic device for collimation and others. The detecting means 45 employs a SSD or the like. The X-ray fluorescence spectrometer 40 includes a transport means 46 such as a robotic arm or manipulator arm and operable to transport the substrate 1 between a cassette 47 within a delivery chamber and the sample table 41.

The transport apparatus 50 includes a transport body in the form of a robotic hand capable of moving forwards and rearwards along a guide rail. This transport apparatus 50 is capable of transporting the substrate 1, when the latter is mounted on a hand portion 50a, from a cassette 3 (a predetermined delivery position) mounted on a cassette support 5 of the spectrometric system towards a decomposing chamber 21 or a recovery chamber 31 of the sample pre-treatment apparatus 10, from the decomposing chamber 21 or the recovery chamber 31 towards the cassette 47 within the delivery chamber of the X-ray fluorescence spectrometer 40, and from the cassette 47 within the delivery chamber back towards the initial cassette 3 placed on the cassette support 5. The cassette support 5 is capable of supporting thereon a plurality of cassettes 3.

The X-ray fluorescence spectrometric system is adapted to be installed so as to extend completely through a partition wall 8 separating between a clean room 6 where a semiconductor manufacturing apparatus or the like is installed, and an analyzing chamber 7 where the semiconductor substrate 1 manufactured in the clean room 6 is analyzed. Only the cassette support 5 is positioned within the clean room. Although not shown, a shutter is provided between the cassette 3 placed on the cassette support 5 and the transport apparatus 50.

The X-ray fluorescence spectrometric system also includes a control apparatus 60 such as, for example, a computer, for controlling the sample pre-treatment apparatus 10, the X-ray fluorescence spectrometer 40, the transport apparatus 50 and the shutter disposed between the cassette 3 placed on the cassette support 5 and the transport apparatus 50, in a common environment (a software). This control apparatus 60 is disposed within, for example, the X-ray fluorescence spectrometer 40. Each of those apparatuses are aggregated together on a common support bench and are all housed within an integral housing.

Of the sample pre-treatment apparatus 10, the vapor phase decomposing apparatus 20 is operable to retain on a surface of the substrate the substance to be measured that is found on the surface of the substrate or the substance to be measured that is found on a surface of a film formed on the surface of the substrate or within the film, after such substance has been dissolved by a reactive gas and has subsequently been dried, in the decomposing chamber 21. The sample recovery apparatus 30 is operable to drop a solution on the substrate having the surface on which the substance to be measures exists, to move the solution on the substrate surface while being retained by a holder, and to retain the substance to be measured on the substrate surface after having been recovered in the solution and then dried, in the recovery chamber 31 that is disposed above the decomposing chamber 21.

Figure 2A:
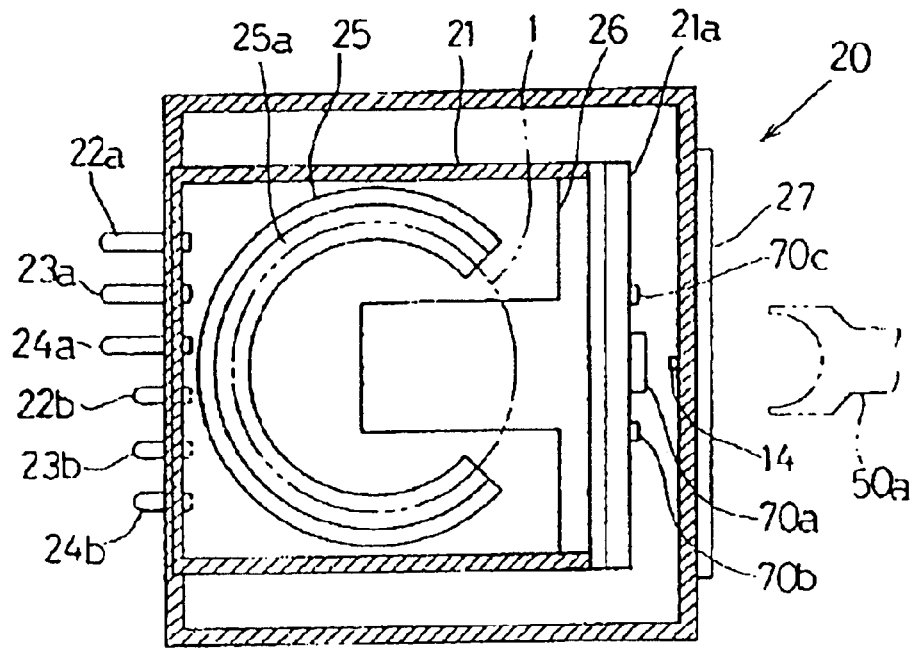
FIG. 2A is a schematic plan view of a vapor phase decomposing apparatus employed in the spectrometric system.
Figure 2B:
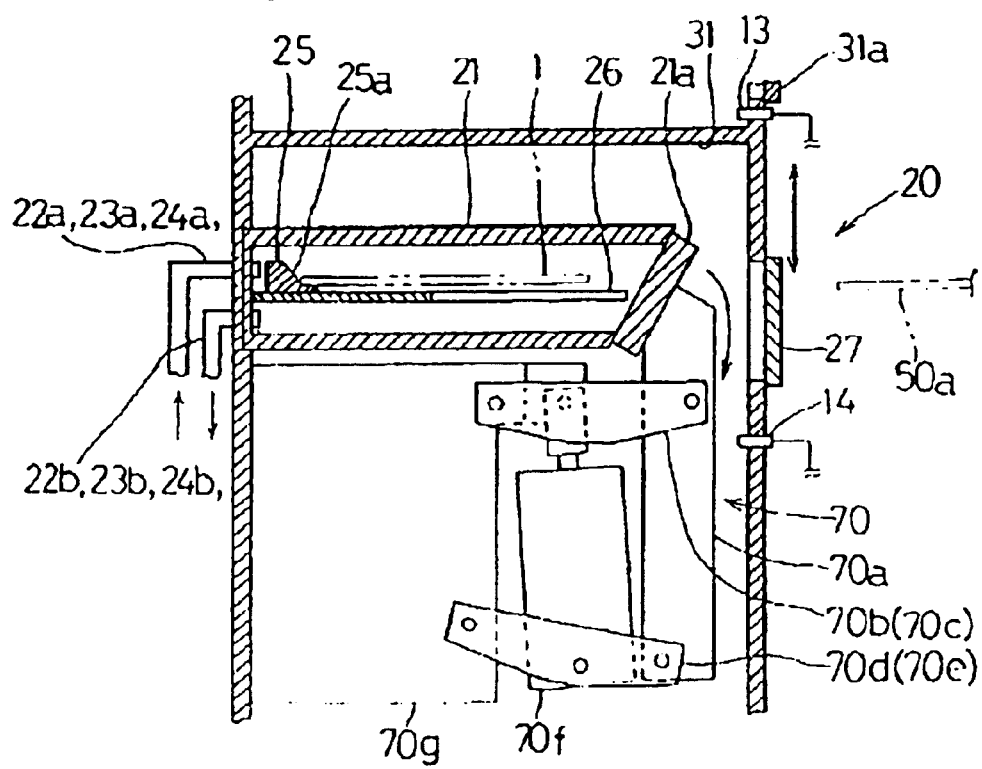
FIG. 2B is a schematic front elevational view of the vapor phase decomposing apparatus shown in FIG. 2A.

The details of the vapor phase decomposing apparatus 20 will be discussed. As shown in FIGS. 2A and 2B, the decomposing chamber 21 of the vapor phase decomposing apparatus 20 is in the form of a box made of, for example, polytetrafluoroethylene (PTFE, trademarked "Teflon") and includes a selectively opening and closing inner shutter 21a positioned on one side confronting the hand portion 50a of the transport apparatus 50. More specifically, the decomposing chamber 21 has its right end opening slantwise downwardly, which opening is adapted to be closed from below by an inner shutter 21a in the form of a generally rectangular plate elongated in a forward and rearward direction.

This inner shutter 21a is selectively opened or closed by an opening and closing mechanism 70 that in the form of a link mechanism made up of a support portion 70a, first to fourth pivot plates 70b, 70c, 70d and 70e, a pneumatic cylinder 70f and a fixture 70g secured fixedly under the decomposing chamber 21 to a wall of the vapor phase decomposing apparatus 20. The support portion 70a is in the form of a square-sectioned pillar member secured to a center portion of an undersurface of the inner shutter 21a. The first and second pivot plates 70b and 70c are paired together and positioned forward and rearward of the support portion 70a with their right ends pivotally connected to an upper portion of the support portion 70a by means of respective pivot pins. The third and fourth pivot plates 70d and 70e are paired together and positioned forward and rearward of the support portion 70a at a location downwardly of the paired first and second pivot plates 70b and 70c with their right ends pivotally connected to a lower portion of the support portion 70a by means of respective pivot pins. On the other hand, respective left ends of the first and second pivot plates 70b and 70c are pivotally connected to an upper portion of the fixture 70g by means of respective pivot pins whereas respective left ends of the third and fourth pivot plates 70d and 70e are pivotally connected to a lower portion of the fixture 70g by means of respective pivot pins.

Figure 3:
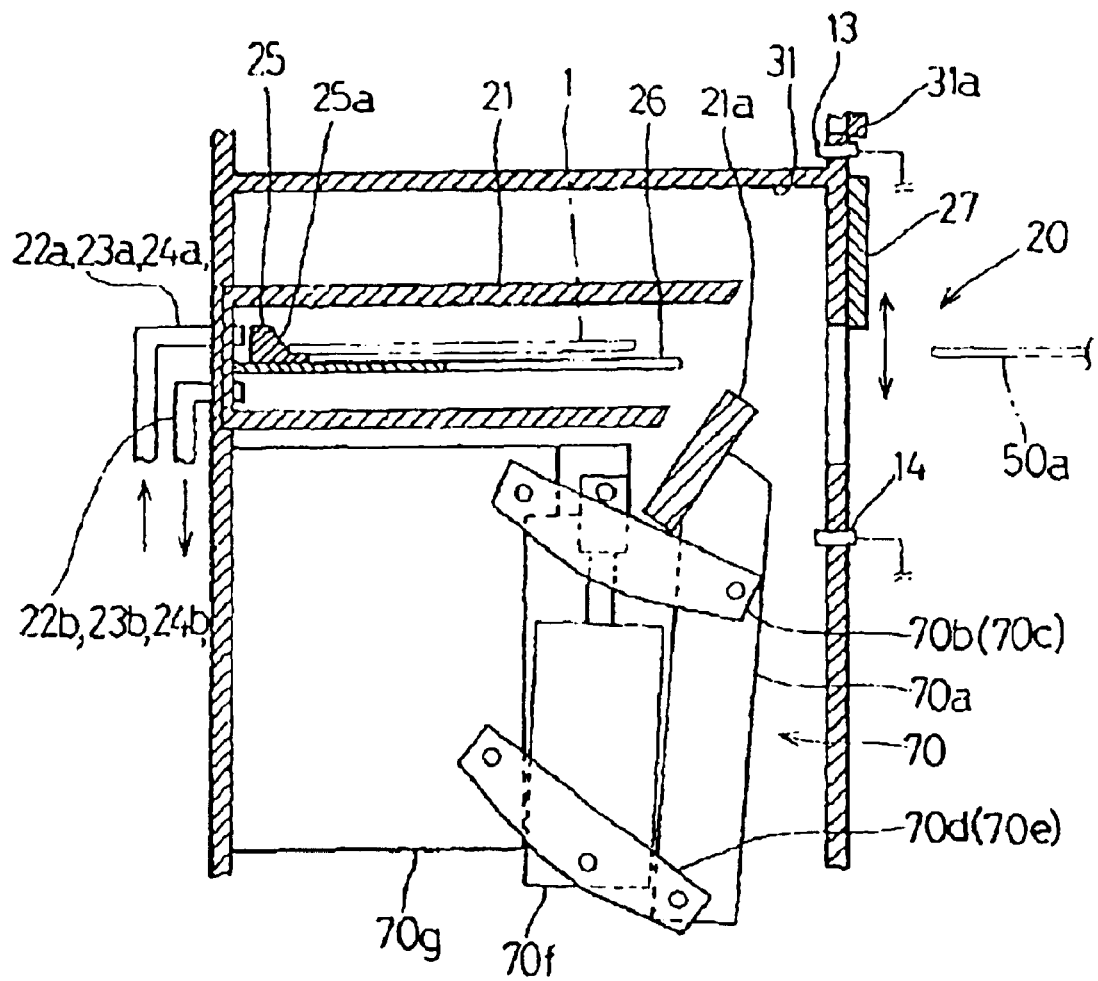
FIG. 3 is a schematic front elevational view of the vapor phase decomposing apparatus shown in a different operative position.

The pneumatic cylinder 70f is interposed between the support portion 70a and the fixture 70g in a left and right direction and has a body thereof pivotally connected at a lower portion thereof with respective intermediate portions of the third and fourth pivot plates 70d and 70e by means of a pivot pin or the like and also has an extendable shaft having a free end thereof pivotally connected with the fixture 70g by means of a pivot pin or the like. Accordingly, when the shaft of the pneumatic cylinder 70f extends, as shown in FIG. 3 in a front elevational view the inner shutter 21a is lowered to open.

With this structural feature, since a box structure defining the decomposing chamber 21 and the inner shutter 21a are not connected with each other mechanically, the box structure can be removed from the vapor phase decomposing apparatus 20 to facilitate cleansing and/or servicing of the box structure outside the vapor phase decomposing apparatus 20.

As best shown in FIG. 2, a selectively opening and closing outer shutter 27 adapted to be selectively opened or closed by an opening and closing mechanism (not shown) is provided at an outer wall of the vapor phase decomposing apparatus 20 at a location spaced from the inner shutter 21a, then closed, through a space in which a stream of air flowing from the recovery chamber 31 defined thereabove can flow downwards. A reactive gas such as, for example, hydrogen fluoride is introduced into the decomposing chamber 21 through a tubing 22a so that not only can an oxide film formed on the surface of the substrate 1 such as, for example, a silicon wafer be dissolved, but the substance to be measured such as a contaminant present on the surface of the film and/or within the film can be dissolved, with an unreacted gas being subsequently discharged through a tubing 22b. Where no film is formed on the surface of the substrate 1, the substance to be measured that is present on the surface of the substrate 1 is dissolved.

The vapor phase decomposing apparatus 20 includes a decomposing chamber cleansing means 23 for flushing an ultra pure water as a cleansing liquid into the decomposing chamber 21 to cleanse the decomposing chamber 21, that is, a cleansing liquid introducing tubing 23a and a discharge tubing 23b. The vapor phase decomposing apparatus 20 also includes a droplet drying means 24 for introducing a clean nitrogen as an inactive gas into the decomposing chamber 21 to purge the hydrogen fluoride and also to dry droplets deposited on the substrate 1, that is, a nitrogen introducing tubing 24a and a discharge tubing 24b. It is to be noted that for the droplet drying means, in place of or in addition to the flow of the inactive gas, the interior of the decomposing chamber may be evacuated to a substantial vacuum to dry the droplets on the substrate. In such case, evacuation and introduction of the inactive gas may be performed repeatedly.

Also, in order for the substrate 1 to be mounted at a predetermined position within the decomposing chamber 21, the vapor phase decomposing apparatus 20 includes a substrate support 25 having its inner periphery tapered as downwardly as at 25a to a narrow width. In other words, the substrate support 25 is in the form of a ring having a portion thereof depleted to avoid any possible interference with the hand portion 50a of the transport apparatus and has its inner periphery formed with a tapered face 25a that represents a downwardly oriented conical surface and is fixed within the decomposing chamber 21 by means of a partition plate 26.

Figure 4A:
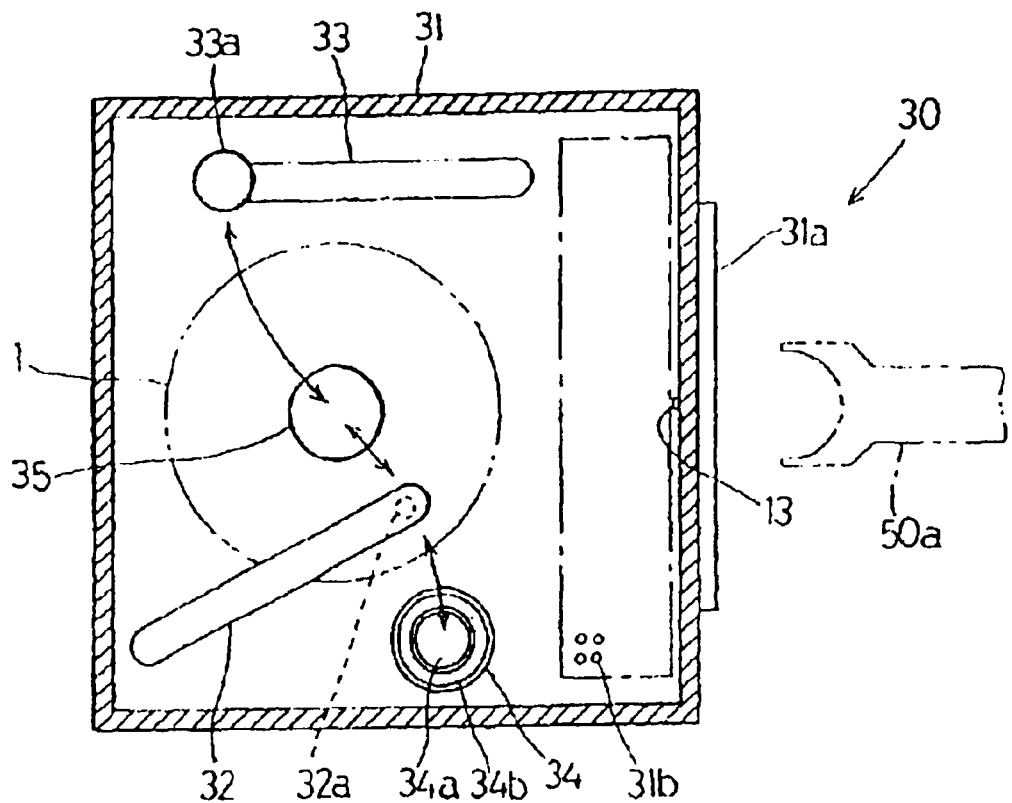
FIG. 4A is a schematic plan view of a sample recovery apparatus employed in the spectrometric system.
Figure 4B:
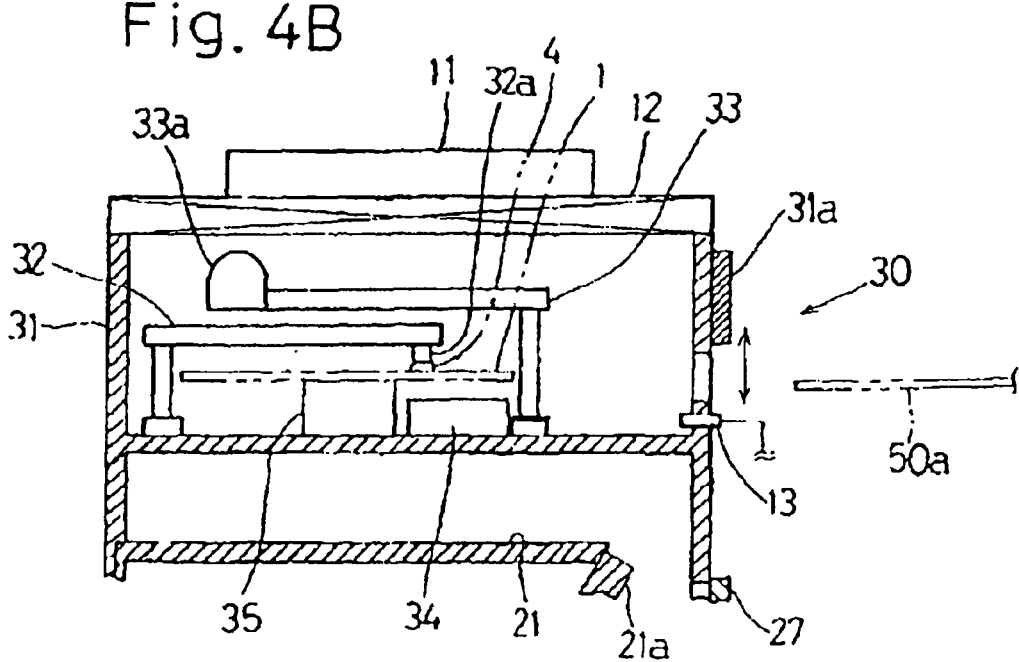
FIG. 4B is a schematic front elevational view of the sample recovery apparatus shown in FIG. 3A.

The details of the sample recovery apparatus 30 will now be described. As shown in FIGS. 4A and 4B, the recovery chamber 31 of the sample recovery apparatus 30 is in the form of a box made of polyvinyl chloride (PVC) and is provided with a fan 11 and a filter 12 both mounted atop the recovery chamber 31. This recovery chamber 31 is disposed above the decomposing chamber 21 and is provided with a selectively opening and closing shutter 31a positioned so as to confront the hand portion 50a of the transport apparatus and adapted to be selectively opened or closed by an opening and closing mechanism (not shown). The recovery chamber 31 has a bottom plate formed with a plurality of punched holes 31b defined at an area adjacent the shutter 31a (encompassed within the single-dotted chain line in FIG. 4A) so that a stream of clean air introduced into the recovery chamber 31 through the filter 12 by means of the fan 11 can flow downwardly and outwardly (rightwards) of the inner shutter 21a of the decomposing chamber 21. (If the inner shutter 21a of the decomposing chamber 21 is opened as shown in FIG. 3, the stream of clean air also falls downwardly and inwardly (leftwards) of the inner shutter 21a.) The sample recovery apparatus 30 includes a recovering solution moving means 32, a recovered solution drying means 33, a retainer cleansing means 34 and a rotary table 35, all of which will subsequently be described.

The recovering solution moving means 32 is in the form of an aim operable to move a retainer 32a, positioned downwardly of a free end of such arm, above the substrate 1 mounted on the rotary table 35 arcuately between an outside of the substrate 1 and a center portion thereof and also operable to move the retainer 32a up and down. The retainer 32a is in the form of a nozzle made of, for example, PTFE, to which a solution (hydrofluoric acid) 4 from a tank positioned further downwardly of the decomposing chamber 21 is supplied. The rotary table 35 is used to support thereon and rotate the substrate 1 in a horizontal plane. In other words, the sample recovery apparatus 30 is so designed and so configured that the hydrofluoric acid solution 4 of a quantity, for example, 100 microlitter that has been dropped from the retainer 32a onto an outer peripheral portion of the substrate 1 can be, while the substrate 1 is being rotated, moved centripetally towards the center of the substrate 1, while the quantity of the hydrofluoric acid solution is sandwiched between the retainer 32a and the substrate 1, so as to recover the substance to be measured that is present on the surface of the substrate 1.

The recovered solution drying means 33 is in the form of an arm operable to move a lamp 33a, provided at a free end of such arm so as to be oriented downwardly, above the substrate 1 arcuately between an outside of the substrate 1 and the center thereof In other words, the sample recovery apparatus 30 is operable to move the lamp 33a towards a position immediately above the center of the substrate 1 and then to heat the solution 4, which has recovered the substance to be measured, to thereby dry it. Even during this drying, the substrate 1 is rotated together with the rotary table 35 in the horizontal plane.

Figure 5A:
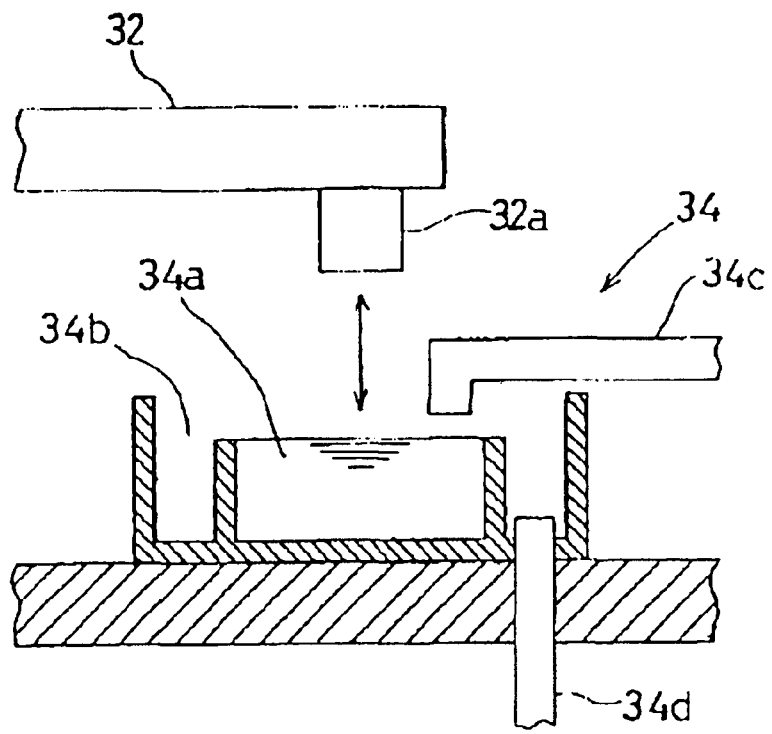
FIG. 5A is a schematic front elevational view of a retainer cleansing means employed in the sample recovery apparatus of the spectrometric system, showing the manner in which a retainer is immersed in a cleansing liquid.
Figure 5B:
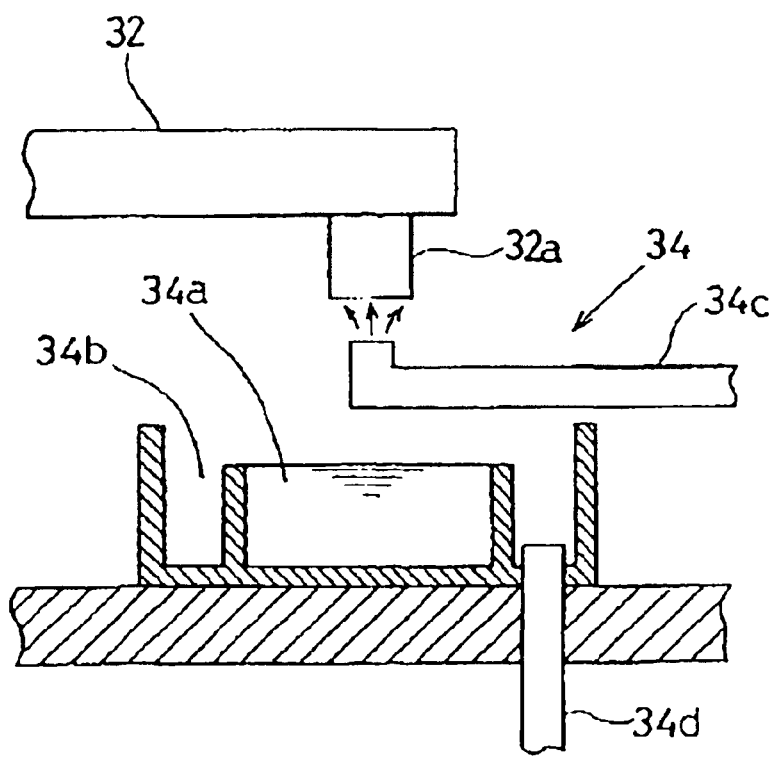
FIG. 5B is a schematic front elevational view of the retainer cleansing means, showing the manner in which the retainer is blown with a cleansing liquid.

The retainer cleansing means 34 is of a structure including as shown in FIG. 5A a vessel including a cylindrical inner bath 34a having a bottom plate and an outer bath 34b of a generally ring shape positioned radially outwardly of the inner bath 34a. This vessel is provided with a supply tubing 34c positioned above the inner bath 34a for supplying a cleansing liquid in the form of an ultra pure water into the inner bath 34a so as to allow the cleansing liquid to overflow the inner bath 34a, and also with a discharge tubing 34d fluid-connected with the bottom of the outer bath 34b for draining the cleansing liquid that has flown over the inner bath 34a. Referring to FIG. 4, the sample recovery apparatus 30 is so designed and so configured that the retainer 32a can be moved by the recovering solution moving means 32 from the outside of the substrate 1 towards a position immediately above the inner bath 34a of the retainer cleansing means 34, that is positioned further outside the outer periphery of the substrate 1, and can then be moved up and down as shown in FIG. 5A. In other words, at least a lower end portion of the retainer 32a is immersed into the cleansing liquid to clean it. The supply tubing 34c is preferably supported in a non-contact fashion with and, hence, separated from the cleansing liquid within the inner bath 34a as shown so that a contaminant contained in the cleansing liquid within the inner bath 34a, which has already been used for cleansing, will not enter the supply tubing 34c. It is to be noted that the cleansing may be effected by blowing the cleansing liquid towards the retainer 32a. In this case, as shown in FIG. 5B, the supply tubing 34c has to be positioned with its open end oriented upwardly so that the cleansing liquid can be blown from below towards the retainer 32a.

As hereinbefore discussed, the vapor phase decomposing apparatus 20 and the sample recovery apparatus 30 altogether constitute the sample preprocessing apparatus 10 and include the automatically opening and closing shutters 21a and 27 and 31a, respectively, as shown in FIG. 2. The vapor phase decomposing apparatus 20 and the sample recovery apparatus 30 also include a differential pressure detecting means 13 (FIG. 4B or FIG. 2B) that is operable to detect the pressure difference between inside and outside of the apparatus 10 (20 and 30), and a concentration detecting means 14 (FIG. 2B) for detecting the concentration of the reactive gas within the apparatus 10. The differential pressure detecting means 13 is, for example, a pressure sensor fitted so as to extend completely across a lower portion of a right wall of the sample recovery apparatus 30 (the sample recovery chamber 31), whereas the concentration detecting means 14 is, for example, a concentration sensor fitted so as to extend completely across a lower portion of a right wall of the vapor phase decomposing apparatus 20 at a location below the decomposing chamber 21 for detecting the hydrogen fluoride.

As hereinbefore described, the vapor phase decomposing apparatus and the sample recovery apparatus 30 are communicated with each other through the punched holes 31b (FIG. 4A) and, accordingly, the both are equal in pressure with each other. Accordingly, the use of the only differential pressure detecting means 13 is sufficient for the apparatuses 20 and 30. Also, since as described hereinbefore the air flows from the sample recovery apparatus 30 (the recovery chamber 31), through the punched holes 31b (FIG. 4A), towards the vapor phase decomposing apparatus 20 (rightwardly of the decomposing chamber 21), mounting of the concentration detecting means 14 to the vapor phase decomposing apparatus 20 is effective to achieve detection of the reactive gas within the sample recovery apparatus 30.

The control apparatus 60 (FIG. 1) when recognizing that the pressure difference detected by the differential pressure detecting means 13 and the concentration detected by the concentration detecting means 14 fall within respective predetermined ranges, causes the automatically opening and closing shutters 21a, 27 and 31a to open. It is to be noted that the sample preprocessing system for the fluorescent X-ray analysis of the present invention is similar to or substantially identical to the above discussed X-ray fluorescence spectrometric system, but the X-ray fluorescence spectrometer 40 and the functions of the transport apparatus 50 and the control apparatus 60 associated with the X-ray fluorescence spectrometer 40 are dispensed with.

In the description that follows, a program employed in the control apparatus 60, shown in FIG. 1, of the X-ray fluorescence spectrometric system of the present invention will be discussed. This program is used to cause the control apparatus 60 to execute one of the following VPD, VPT and TXRF modes according to a selection made by an operator. In the VPD mode, the transport apparatus 50 is caused to transport the substrate 1 from the predetermined delivery position towards the decomposing chamber 21. Subsequently, the vapor phase decomposing apparatus 20 is caused to introduce the reactive gas into the decomposing chamber 21, which gas is purged out of the decomposing chamber 21 a predetermined time thereafter. Then, the transport apparatus 50 is caused to transport the substrate 1 towards the recovery chamber 31. Next, the sample recovery apparatus 30 shown in FIG. 4 is caused to drop the solution 4 onto the substrate 1. After it, the sample recovery apparatus 30 is caused to move the dropped solution 4, while being retained by the retainer 32a, along a surface of the substrate 1 and then to recover the substance to be measured. Thereafter, the sample recovery apparatus 30 is caused to dry the substance to be measured. Next, the transport apparatus 50 shown in FIG. 1 is caused to transport the substrate 1 towards the X-ray fluorescence spectrometer 40. Thereafter, the X-ray fluorescence spectrometer 40 is caused to measure intensities of fluorescent X-rays 44 emitted from the substance to be measured in response to irradiation thereof with primary X-rays 43. Thereafter, the transport apparatus 50 is caused to transport the substrate 1 back towards the delivery position.

In the VPT mode, the transport apparatus 50 is in the first place caused to transport the substrate 1 from the predetermined delivery position towards the decomposing chamber 21. After it, the vapor phase decomposing apparatus 20 is caused to introduce the reactive gas into the decomposing chamber 21, which gas is purged out of the decomposing chamber 21 a predetermined time thereafter. Then, the transport apparatus 50 is caused to transport the substrate 1 towards the X-ray fluorescence spectrometer 40. Thereafter, the X-ray fluorescence spectrometer 40 is caused to measure intensities of fluorescent X-rays 44 emitted from the substance to be measured in response to irradiation thereof with primary X-rays 43. Thereafter, the transport apparatus 50 is caused to transport the substrate 1 back towards the delivery position.

In the TXRF mode, the transport apparatus 50 is in the first place caused to transport the substrate 1 from the predetermined delivery position towards the X-ray fluorescence spectrometer 40. After it, the X-ray fluorescence spectrometer 40 is caused to measure intensities of fluorescent X-rays 44 emitted from the substance to be measured in response to irradiation thereof with primary X-rays 43. Thereafter, the transport apparatus 50 is caused to transport the substrate 1 back towards the delivery position.

The operation of the X-ray fluorescence spectrometric system will now be described. Within the clean room shown in FIG. 1, when the cassette 3 accommodating therein the substrates 1, for example, silicone wafers containing a contaminant to be analyzed are mounted on the cassette support 5 and an instruction to preprocess and analyze the substrate 1 within the cassette 3 (the predetermined delivery position) under a predetermined condition is subsequently inputted from an input means (not shown) to the control apparatus 60, the various apparatus and the spectrometer of the X-ray fluorescence spectrometric system can be controlled to perform as follows. Since the preprocessing and analyzing conditions can be set for each substrate 1 by means of the input means (not shown) while the operator looks at a display means (not shown) of the control apparatus 60 and the sample pre-treatment apparatus 10, the X-ray fluorescence spectrometer 40 and the transport apparatus 60 can be controlled in a common environment, the X-ray fluorescence spectrometric system as a whole is easy to operate.

In the X-ray fluorescence spectrometric system of the present invention, as the preprocessing and analyzing conditions, three modes, i.e., VPD, VPT and TXRF modes are available and the operation of the spectrometric system under the VPD (vapor phase decomposition) mode will first be described.

At the outset, the transport apparatus 50 transports the substrate 1 towards the decomposing chamber 21 and places it on the substrate support 25 as shown in FIG. 2. At the time of delivery, the automatically opening and closing shutters 21a and 27 of the vapor phase decomposing chamber 20 are opened. More specifically, the control apparatus (FIG. 1) first recognizes that the pressure difference detected by the differential pressure detecting means 13 is within the predetermined range, for example, the inside pressure of the vapor phase decomposing apparatus 20 is lower than the outside pressure of the apparatus 20, and then opens the automatically opening and closing shutter 21a. If the inside pressure of the vapor phase decomposing apparatus 20 is not lower than the outside pressure of the apparatus 20, an error indication is issued and the automatically opening and closing shutter 21a will not be opened. This is for the purpose of avoiding the possibility that if the automatically opening and closing shutter 21a is opened while a substantial concentration of the hydrogen fluoride remains within the decomposing chamber 21 and the inside pressure of the apparatus 20 is not lower than the pressure outside the apparatus 20, the stream of air flowing from the outside of the sample preprocessing apparatus 10 (20 and 30) and then past the recovery chamber 31 will not be properly formed by the effect of the pressure difference and the hydrogen fluoride emerging from the decomposing chamber 21 will stagnate and, further, if sealing thereof is insufficient even though the automatically opening and closing shutter 27 is closed, there is the possibility that it will flow outwardly of the sample preprocessing apparatus 10.

Then, after the control apparatus 60 has confirmed that the inside pressure of the vapor phase decomposing apparatus 20 is lower than the pressure outside the apparatus 20 and the concentration of the hydrogen fluoride detected by the concentration detecting means 14 is within the predetermined range, for example, not higher than a predetermined value, the automatically opening and closing shutter 27 is opened. If the inside pressure of the vapor phase decomposing apparatus 20 is not lower than the pressure outside the apparatus 20 or the concentration of the hydrogen fluoride is higher than the predetermined value, an error indication is issued and the automatically opening and closing shutter 27 will not be opened.

Thus, the control apparatus 60 (FIG. 1) after having confirmed that the pressure difference between inside and outside of the sample preprocessing apparatus 10 (20 and 30) and the concentration of the reactive gas within the sample preprocessing apparatus 10 are within the respective predetermined ranges causes the automatically opening and closing shutters 21a and 27 to open. Accordingly, there is no possibility that the reactive gas will flow from the sample preprocessing apparatus 10 to the outside and, therefore, a possible corrosion of the transport apparatus 50 and others positioned outside thereof can be avoided to thereby increase the servicing lifetime thereof.

Also, since the substrate support 25 has its inner periphery formed with the downwardly narrowed taper 25a, even though the substrate 1 is somewhat displaced from a predetermined position on the hand portion 50a, mere placement of the substrate 1 on the substrate support 25 is effective to allow the substrate 1 to be slipped onto the substrate support 25 by the effect of its own weight and, hence, to be properly positioned and, accordingly, the subsequent recovery and analysis can be accurately performed. After the transport of the substrate, the automatically opening and closing shutters 21a and 27 of the vapor phase decomposing apparatus 20 are closed.

The hydrogen fluoride is then introduced through the tubing 22a into the sealed decomposing chamber 21 with the automatically opening and closing shutters 21a and 27 closed, to thereby dissolve the oxide film formed on the surface of the substrate 1 and also to dissolve the substance to be measured such as the contaminant present on the surface of the film and/or within the film, and the hydrogen fluoride is subsequently discharged through the tubing 22b. Where no film is formed on the surface of the substrate 1, the substance to be measured that is present on the surface of the substrate 1 is dissolved. At the time of introduction of the hydrogen fluoride, it is preferred that a valve on the discharge tubing 22b is opened prior to opening of a valve on the introducing tubing 22a, but this is not always essential, and the reverse or the synchronous opening may be acceptable. The vapor phase decomposition by this hydrogen fluoride is performed for, for example, 10 minutes which can be set.

After a predetermined length of time during which the vapor phase decomposition is performed, nitrogen is allowed to flow by the droplet drying means 24 while the decomposing chamber 21 is evacuated, resulting in purge of the hydrogen fluoride and, at the same time, the droplets formed on the substrate 1 can be dried. In this way, during the subsequent transport, the hand portion 50a of the transport apparatus will not be brought into contact with the droplets and will not therefore be corroded and, therefore, there is no possibility that the transport will be inaccurate, which would otherwise occur when the substrate 1 undergoes slippage on the hand portion 50a. Also, there is no possibility that the hydrogen fluoride may constitute a cause of corrosion which would occur when it flow into the transport apparatus 50 and/or the X-ray fluorescence spectrometer 40 (FIG. 1). Also, the decomposing chamber 21 is routinely cleansed with the ultra pure water by the decomposing chamber cleansing means 23. In this way, since the cleansing of the interior of the decomposing chamber 21 as well is automated, the system can be further easily operated.

In the next place, the transport apparatus 50 transports the substrate 1 towards the recovery chamber 3 shown in FIG. 4 so that the substrate 1 can be placed on the rotary table 35 with its center aligned with the center of rotation of the rotary table 35. At the time of this transport, the automatically opening and closing shutters 21a, 27 and 31a of the vapor phase decomposing apparatus 20 and the sample recovery apparatus 30 are automatically opened. More specifically, as is the case when the substrate 1 is transported towards the decomposing chamber 21, the control apparatus 60 (FIG. 1) after having first confirmed that the inside pressure of the vapor phase decomposing apparatus 20 (FIG. 2) is lower than the pressure outside the apparatus 20 causes the automatically opening and closing shutter 21a to open. If the inside pressure of the vapor phase decomposing apparatus 20 is not lower than the pressure outside the apparatus 20, an error indication is issued and the automatically opening and closing shutter 21a will not be opened. Thereafter, the control apparatus 60 refers to the pressure difference detected by the differential pressure detecting means 13 to confirm that the inside pressure of the vapor phase decomposing apparatus 20 is lower than the pressure outside the apparatus 20 and also refers to the concentration of the hydrogen fluoride detected by the concentration detecting means 14 (FIG. 2) to confirm that the concentration of the hydrogen fluoride is not higher than the predetermined value, wherefore the automatically opening and closing shutters 27 and 31a are opened. If the inside pressure of the vapor phase decomposing apparatus 20 is not lower than the pressure outside the apparatus 20, or if the concentration of the hydrogen fluoride is higher than the predetermined value, an error indication is issued and the automatically opening and closing shutters 27 and 31a will not be opened. After the transport of the substrate 1, the automatically opening and closing shutters 21a, 27 and 31a are closed.

In this way, since the transport of the substrate 1 from the decomposing chamber 21 towards the recovery chamber 31 is carried out by the transport apparatus 50, a possible contamination in contact with operator's hands can be avoided and an accurate analysis can be attained. Also, since the control apparatus 60 (FIG. 1) causes the automatically opening and closing shutters 21a, 27 and 31a to open after having confirmed that the pressure difference between inside and outside of the sample preprocessing apparatus 10 (20 and 30) and the concentration of the reactive gas within the sample preprocessing apparatus 10 are within the respective predetermined ranges, there is no possibility that the reactive gas will flow from the sample preprocessing apparatus 10 to the outside and, therefore, a possible corrosion of the transport apparatus 50 and others positioned outside thereof can be avoided to thereby increase the servicing lifetime thereof.

Thereafter, the sample recovery apparatus 30 moves the hydrofluoric acid solution 4, which has been dropped from the retainer 32a onto an outer peripheral portion of the substrate 1, towards the center of the substrate 1 while the substrate 1 is rotated and the hydrofluoric acid solution 4 is retained by the retainer 32a to thereby recover the substance to be measured present on the surface of the substrate 1 (i.e., the substance to be measured that is retained by the vapor phase decomposing apparatus 20 on the surface of the substrate 1). The position at which the hydrofluoric acid solution 4 is dropped and the path of movement of the retainer 32a during the recovery process may not be limited to those described above and variants thereof can be contemplated. After the recovery, the retainer 32a is elevated and moved to a position above the inner bath 34a of the retainer cleansing means 34 and is then immersed into the cleansing liquid to cleanse it. In this way, cleansing of the retainer 32a is also automated and, accordingly, the X-ray fluorescence spectrometric system can be further easy to operate.

Then, the sample recovery apparatus 30 move the lamp 33a to a position immediately above the center of the substrate 1 to heat the solution 4, which has recovered the substance to be measured, to thereby dry the substance to be measured. Even during this drying, the substrate 1 is rotated in the horizontal plane together with the rotary table 35. Accordingly, since there is no possibility that the substance to be measured may be disproportionately dried and spread, a further accurate analysis is possible. Also, since the recovery chamber 31 is arranged above the decomposing chamber 21 and a stream of clean air flowing into the recovery chamber 31 through the filter 12 by means of the fan 11 flows through the punched holes 31b into a space outwardly of the inner shutter 21a of the decomposing shutter 21a, the X-ray fluorescence spectrometric system as a whole can be installed in a sufficiently reduced space for installation and, also, the recovery chamber 31 can be kept clean. It is to be noted that one of the cleansing of the retainer 32a and the drying of the substance to be measured can be performed prior to the other as desired or the both may be performed in parallel to each other, provided that they are performed after the retainer 32a has been retracted away from the position immediately above the solution 4 which has recovered the substance to be measured.

Subsequently, as shown in FIG. 1, the transport apparatus 50 transports the substrate 1, which has recovered the substance 2 to be measured, towards the cassette 47 within a delivery chamber of the X-ray fluorescence spectrometer 40. During this transport, the automatically opening and closing shutter 31a, as shown in FIG. 4, of the sample recovery apparatus 30 is automatically opened. More specifically, the control apparatus 60 (FIG. 1) after having first confirmed that the inside pressure of the sample recovery apparatus 30 is lower than the pressure outside the apparatus 30 and that the concentration of the hydrogen fluoride detected by the concentration detecting means 14 (FIG. 2) is not higher than the predetermined value causes the automatically opening and closing shutter 31a to open. If the inside pressure of the sample recovery apparatus 30 is not lower than the pressure outside the apparatus 30, or the concentration of the hydrogen fluoride is higher than the predetermined value, an error indication is issued and the automatically opening and closing shutter 31a will not be opened. After the transport of the substrate 1, the automatically opening and closing shutter 31a is closed.

In this way, since the control apparatus 60 (FIG. 1) after having confirmed that the pressure difference between inside and outside of the sample preprocessing apparatus 10 (20 and 30) and the concentration of the reactive gas within the sample preprocessing apparatus 10 are within the respective predetermined ranges causes the automatically opening and closing shutter 31a to open, there is no possibility that the reactive gas will flow from the sample preprocessing apparatus 10 to the outside and, therefore, a possible corrosion of the transport apparatus 50 and others positioned outside thereof can be avoided to thereby increase the servicing lifetime thereof.

Thereafter, the X-ray fluorescence spectrometer 40 shown in FIG. 1, after the substrate 1 has been transported to the sample table 41 by the transport means 46, performs a total reflection fluorescent X-ray analysis. After the analysis, the substrate 1 is transported by the transport means 46 towards the cassette 47 within the delivery chamber and is then transported by the transport apparatus 50 towards the initial cassette 3 placed on the cassette support 5. It is to be noted that if during the initial analysis of the substrate 1, recovery of the next succeeding substrate and decomposition of the succeeding substrate after next are performed simultaneously, the overall preprocessing and the analyzing work can be quickly accomplished.

While the foregoing is an explanation of the X-ray fluorescence spectrometric system under the VPD (vapor phase decomposition) mode, the operation of the spectrometric system under the VPT (vapor phase treatment) mode will now be described. Since under this VPT mode no recovery of the substance to be measured is carried out by the sample recovery apparatus 30, the substance to be measured is not concentrated and the sensitivity of the analysis will not increase so much as that under the VPD mode, but a distribution of the substance to be measured on the substrate can be ascertained. Also, even under the VPT mode, the substance to be measured can be transformed into finely divided particles as it is dried after having been dissolved by the vapor phase decomposing apparatus 20 in contact with hydrogen fluoride and, accordingly, the sensitivity during the total reflection fluorescent X-ray analysis can be increased.

The operation of the spectrometric system under the VPT mode is similar to that under the VPD mode so far as the process is concerned to a stage, in which within the vapor phase decomposing apparatus 20 shown in FIG. 2, the decomposing chamber 21 is evacuated while being supplied with nitrogen by the droplet drying means 24, with the hydrogen fluoride being purged, and the droplets formed on the substrate 1 are dried. Under this VPT mode, subsequent to the drying, the transport apparatus 50 transports the substrate 1, then retaining the substance 2 to be measured, towards the cassette 47 (FIG. 1) within the delivery chamber of the X-ray fluorescence spectrometer 40. At the time of this transport, the automatically opening and closing shutters 21a and 27 of the vapor phase decomposing apparatus 20 are automatically opened.

More specifically, as is the case when the substrate 1 is transported towards the recovery chamber 31 under the VPD mode, the control apparatus 60 (FIG. 1) after having first confirmed that the inside pressure of the vapor phase decomposing apparatus 20 is lower than the pressure outside the apparatus 20 causes the automatically opening and closing shutter 21a to open. If the inside pressure of the vapor phase decomposing apparatus 20 is not lower than the pressure outside the apparatus 20, an error indication is issued and the automatically opening and closing shutter 21a will not be opened. Thereafter, the control apparatus 60 confirms that the inside pressure of the vapor phase decomposing apparatus 20 is lower than the pressure outside the apparatus 20 and that the concentration of the hydrogen fluoride is not higher than the predetermined value, causes the automatically opening and closing shutter 27 to open. If the inside pressure of the vapor phase decomposing apparatus 20 is not lower than the pressure outside the apparatus 20, or if the concentration of the hydrogen fluoride is higher than the predetermined value, an error indication is issued and the automatically opening and closing shutter 27 will not be opened. After the transport of the substrate 1, the automatically opening and closing shutters 21a and 27 of the vapor phase decomposing apparatus 20 are closed.

In this way, since the control apparatus 60 (FIG. 1) causes the automatically opening and closing shutters 21a and 27 to open after having confirmed that the pressure difference between inside and outside of the sample preprocessing apparatus 10 (20 and 30) and the concentration of the reactive gas within the sample preprocessing apparatus 10 are within the respective predetermined ranges, there is no possibility that the reactive gas will flow from the sample preprocessing apparatus 10 to the outside and, therefore, a possible corrosion of the transport apparatus 50 and others positioned outside thereof can be avoided to thereby increase the servicing lifetime thereof. Thereafter, the analysis by the X-ray fluorescence spectrometer 40 and the transport back to the initial cassette 3 by the transport apparatus 50 are performed in a manner similar to those under the VPD mode.

Under the TXRF mode, the vapor phase decomposition as well is not performed by the vapor phase decomposing apparatus 20, that is, the preprocessing by the sample pre-treatment apparatus 10 is not performed. This corresponds to the substrate (sample) 1 that does not require the preprocessing and, under this mode, the transport apparatus 50 transports the substrate 1 from the cassette 3, placed on the cassette support 5, towards the cassette 47 within the delivery chamber of the X-ray fluorescence spectrometer 40. Thereafter, analysis by the X-ray fluorescence spectrometer 50 and transport of the substrate 1 back to the initial cassette 3 by the transport apparatus 50 are performed sequentially in a manner similar to those under the VPD mode. In other words, the X-ray fluorescence spectrometric system functions as the standard total reflection X-ray fluorescence spectrometer.

Other than those described above, where no oxide film is formed on the substrate 1 and no dissolution of the film is required, it is possible to set under a DADD (direct acid droplet decomposition) mode under which during the sample preprocessing only recovery of the substance to be measured is carried out by the sample recovery apparatus 30. Under this DADD mode, the transport apparatus 50 transports the substrate 1 from the cassette 3 placed on the cassette support 5 towards the recovery chamber 31 of the sample recovery apparatus 30. At the time of this transport of the substrate 1, the automatically opening and closing shutter 31a of the sample recovery apparatus 30 of FIG. 4 is opened.

More specifically, the control apparatus 60 (FIG. 1) refers to the pressure difference detected by the differential pressure detecting means 13 to confirm that the inside pressure of the sample recovery apparatus 30 is lower than the pressure outside the apparatus 30 and refers to the concentration detected by the concentration detecting means 14 (FIG. 2) to confirm that the concentration of the hydrogen fluoride is not higher than the predetermined value, causes the automatically opening and closing shutter 31a to open. If the inside pressure of the sample recovery apparatus 30 is not lower than the pressure outside the apparatus 30 or the concentration of the hydrogen fluoride is higher than the predetermined value, an error indication is issued and the automatically opening and closing shutter 31a will not be opened. After the transport of the substrate, the automatically opening and closing shutter 31a is closed.

Even in this case, since the control apparatus 60 (FIG. 1) causes the automatically opening and closing shutter 31a to open after having confirmed that the pressure difference between inside and outside of the sample preprocessing apparatus 10 (20 and 30) and the concentration of the reactive gas within the sample preprocessing apparatus 10 are within the respective predetermined ranges, there is no possibility that the reactive gas will flow from the sample preprocessing apparatus 10 to the outside and, therefore, a possible corrosion of the transport apparatus 50 and others positioned outside thereof can be avoided to thereby increase the servicing lifetime thereof. Subsequently, recovery of the substance to be measured, cleansing of the retainer 32a and drying of the substance to be measured by the sample recovery apparatus 30, transport of the substrate 1 by the transport apparatus 50 towards the cassette 47 within the delivery chamber of the X-ray fluorescence apparatus 40, analysis by the X-ray fluorescence spectrometer 40, and transport of the substrate 1 by the transport apparatus 50 back to the initial cassette 3 are sequentially performed in a manner similar to those under the VPD mode.

While the X-ray fluorescence spectrometric system and the sample preprocessing system for the fluorescent X-ray analysis shown and described in connection with the preferred embodiment of the present invention has been described including the sample recovery apparatus 30 positioned above the vapor phase decomposing apparatus 20 so that the recovery chamber 31 can occupy a position above the decomposing chamber 21, the present invention is not always limited thereto and the vapor phase decomposing apparatus 20 and the sample recovery apparatus 30 may be reversed in position relative to each other or can be arranged in side-by-side fashion in a horizontal direction. It is, however, to be noted that regardless of how they are arranged, and if the apparatuses 20 and 30 are not communicated with each other with no air flowing therebetween, the differential pressure detecting means 13 and the concentration detecting means 14 have to be provided for each of the apparatuses 20 and 30.

Although the present invention has been fully described in connection with the preferred embodiments thereof with reference to the accompanying drawings which are used only for the purpose of illustration, those skilled in the art will readily conceive numerous changes and modifications within the framework of obviousness upon the reading of the specification herein presented of the present invention. Accordingly, such changes and modifications are, unless they depart from the scope of the present invention as delivered from the claims annexed hereto, to be construed as included therein.

What is claimed is:

1. A sample preprocessing system for a fluorescent X-ray analysis which comprises:

a vapor phase decomposing apparatus operable to retain on a surface of a substrate a substance to be measured that is found on the surface of the substrate or a substance to be measured that is found on a surface of a film formed on the surface of the substrate or within the film, after such substance has been dissolved by a reactive gas and has subsequently been dried, in a decomposing chamber;

a sample recovery apparatus operable to drop a solution on the substrate having the surface on which the substance to be measures exists, to move the solution on the substrate surface while being retained by a holder, and to retain the substance to be measured on the substrate surface after having been recovered in the solution and then dried, in a recovery chamber;

a transport apparatus operable to transport the substrate from the decomposing chamber towards the recovery chamber; and a control apparatus for controlling the vapor phase decomposing apparatus, the sample recovery apparatus, and the transport apparatus;

wherein a set of the vapor phase decomposing apparatus and the sample recovery apparatus has an automatically opening and closing shutter, a differential pressure detecting means for detecting a pressure difference between inside and outside of the set and a concentration detecting means for detecting a concentration of the reactive gas within the set; and wherein the control apparatus after having confirmed that the pressure difference detected by the differential pressure detecting means and the concentration detected by the concentration detecting means are within respective predetermined ranges causes the automatically opening and closing shutter to open.

2. An X-ray fluorescence spectrometric system which comprises:

a sample preprocessing system for a fluorescent X-ray analysis as defined in claim 1; and an X-ray fluorescence spectrometer operable to measure intensities of fluorescent X-rays emitted from the substance to be measured that is retained on the substrate by the vapor phase decomposing apparatus or the sample recovery apparatus, when such substance is irradiated by primary X-rays;

wherein the transport apparatus is also operable to transport the substrate from the decomposing chamber towards the X-ray fluorescence spectrometer and from the recovery chamber towards the X-ray fluorescence spectrometer; and wherein the control apparatus also controls the X-ray fluorescence spectrometer.

3. The sample preprocessing system for the Fluorescent X-ray analysis as claimed in claim 1, wherein the vapor phase decomposing apparatus and the sample recovery apparatus are communicated with each other and the differential pressure detecting means comprises a single pressure sensor fitted to the vapor phase decomposing apparatus or the sample recovery apparatus.

4. The sample preprocessing system for the Fluorescent X-ray analysis as claimed in claim 1, wherein the recovery chamber is disposed above the decomposing chamber to allow air inside the sample recovery apparatus to flow into the vapor phase decomposing apparatus and wherein the concentration detecting means comprises a single hydrogen fluoride concentration sensor fitted to the vapor phase decomposing apparatus.

* * * * *